United States Patent [19]

Nalepa

[11] Patent Number: 4,476,332

[45] Date of Patent: Oct. 9, 1984

[54] PREPARATION OF ALKANEDIOLS

[75] Inventor: Christopher J. Nalepa, Baton Rouge, La.

[73] Assignee: Ethyl Corporation, Richmond, Va.

[21] Appl. No.: 564,089

[22] Filed: Dec. 21, 1983

[51] Int. Cl.³ .................. C07C 29/132; C07C 33/26; C07C 67/00; C07C 59/245
[52] U.S. Cl. .................. 568/865; 260/465.6; 560/263; 562/582; 568/807
[58] Field of Search ................ 568/865, 807; 562/582; 560/263; 260/465.6

[56] References Cited

U.S. PATENT DOCUMENTS

| | | | |
|---|---|---|---|
| 2,546,019 | 3/1951 | Smith | 568/865 |
| 2,888,492 | 5/1959 | Fischer et al. | 568/865 |
| 3,760,011 | 9/1973 | Robinson et al. | 568/865 |
| 4,146,741 | 3/1979 | Prichard | 568/865 |

FOREIGN PATENT DOCUMENTS

| | | | |
|---|---|---|---|
| 527170 | 7/1956 | Canada | 568/865 |
| 673367 | 10/1963 | Canada | 568/865 |

OTHER PUBLICATIONS

Watson; James M., "Butane-1,4-diol from Hydrolytic Reduction of Furan", Ind. Eng. Chem. Prod. Res. Develop., 12, (4), 310-311, (1973).

Primary Examiner—J. E. Evans
Attorney, Agent, or Firm—Donald L. Johnson; John F. Sieberth; Teresa M. Stanek

[57] ABSTRACT

Disclosed is an improved process for producing alkanediols by the hydrolytic reduction of hydrolytically reducible furans. The improvement comprises utilizing a supported ruthenium catalyst, and trihaloacetic acid or a mixture thereof as a promoter for the hydrolytic reduction. The hydrolytic reduction is conducted in an aqueous medium at elevated temperatures and elevated pressures.

20 Claims, No Drawings

PREPARATION OF ALKANEDIOLS

FIELD OF THE INVENTION

This case relates to a process for the preparation of a 1,4-butanediol from a furan.

BACKGROUND OF THE INVENTION

Furan has been hydrogenated in a neutral or weakly acid aqueous system in the presence of a nickel catalyst as shown by Russian Pat. No. 114,928 (1958) to P. A. Moshkin et al. to produce 1,4-butanediol, tetrahydrofuran and small amounts of butanol. One example shows the inclusion of a small amount of formic acid in the reaction mixture. James M. Watson, Ind. Eng. Chem. Prod. Res. Develop. 12 (4) 310-311 (1973) shows the same general reaction where acetic acid is present in the reaction mixture. The Watson publication also discloses that the reduction of furan under various conditions using Ni, Pd, Pt and Ru catalysts has generally been reported to give either tetrahydrofuran or 1-butanol or mixtures thereof (Rylander, 1967; Augustine, 1965; Smith & Fuzek, 1949). In both processes, the yield of 1,4-butanediol is not as high as could be desired and unwanted by-products are produced, such as the mono- and diformate, and mono- and diacetate esters of 1,4-butanediol. These esters have boiling points quite close to the boiling point of 1,4-butanediol itself and it is expensive and difficult to distill them off; in fact, the diacetate ester of 1,4-butanediol has the same boiling point as 1,4-butanediol and cannot be separated by distillation. Accordingly, the 1,4-butanediol produced by these processes contains the esters as impurities. Pure, "polymer grade" 1,4-butanediol is necessary in the manufacture of useful high molecular weight polyesters from terephthalic acid. Therefore, the impure diol produced by the above-mentioned prior art processes cannot be used directly.

A welcome contribution to the art would be a process that produces 1,4-butanediol in good yields, without substantial impurities which cannot be easily separated from the highly desired 1,4-butanediol.

THE INVENTION

This invention provides an improved process for the production of alkanediols in which the two hydroxy groups resulting from the hydrolytic reduction are bonded to different carbon atoms which are separated by two other carbon atoms—i.e., the two hydroxy groups resulting from the hydrolytic reduction are in a "1,4" position relative to each other—by the hydrolytic reduction of hydrolytically reducible furans at elevated temperatures and elevated pressures using a supported metal catalyst. The improvement comprises conducting the hydrolytic reduction in an aqueous medium utilizing a supported ruthenium catalyst, and a trihaloacetic acid, preferably trifluoroacetic acid or trihalochloroacetic acid or a mixture thereof as promoter for the hydrolytic reduction.

The hydrolytically reducible furans utilizable in the process of this invention are furan and any substituted furan whose substituent(s) are inert under the reaction conditions. In general the furans are represented by the formula:

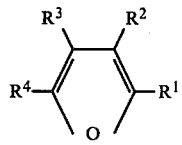

wherein $R^1$, $R^2$, $R^3$ and $R^4$ are the same or different aliphatic or aromatic group(s) or hydrogen atom(s). Examples of the substituent groups include, but are not limited to: hydrocarbyl groups, such as, alkyl, aryl, and the like; carboxylic acid derived groups; alkanol derived groups, such as, hydroxyalkyl, e.g., $-CH_2OH$, and the like; alkenyl derived groups, such as, those groups derived from, for example, acrylonitrile, e.g., $-CH=CH-CN$, and the like. Examples of substituted furans include, but are not limited to: 2-methylfuran, 2,5-dimethylfuran, 2,5-diphenylfuran, 3-methylfuran, 2-acetylfuran, 3,4-bis(acetoxymethyl)furan, 2-furanacrylonitrile, 3,4-furandicarboxylic acid, 2,5-furandimethanol, 3-furanmethanol, and the like.

The furan used will, of course, determine the alkanediol product obtained by the process of this invention. Preferably, the process of this invention is utilized to produce 1,4-butanediol and substituted 1,4-butanediols. Thus, for example, 1,4-butanediol is obtained from furan; 1-methyl-1,4-butanediol (1,4-pentanediol) from 2-methylfuran; 1,4-dimethyl-1,4-butanediol (2,5-hexanediol) from 2,5-dimethylfuran; and the like.

The catalysts utilized are composed of ruthenium (Ru) on inert carriers or supports. Any carrier or support may be used as long as it is inert under the reaction conditions. Examples of these supports may include, for example, $Al_2O_3-SiO_2$, diatomaceous earth, finely divided silica, activated carbon, and the like. A preferred carrier is $Al_2O_3-SiO_2$. The amount of ruthenium on the support is not critical to the reaction, however, catalysts containing 0.5% by weight to about 20% by weight of ruthenium, based on the weight of the catalyst are preferred, with about 5% by weight to about 10% by weight being more preferred, and about 5% by weight being most preferred. Supported ruthenium catalysts are commercially available, for example, Aldrich Chemical Co. and Alfa-Ventron. The catalyst to furan weight ratio is within the range of from about 1:3 (catalyst:furan) to about 1:50 with from about 1:7 to about 1:30 being preferred and about 1:15 being most preferred. The catalyst is used with a trihaloacetic acid, preferably trifluoroacetic acid or trichloroacetic acid or a mixture thereof as the promoter for the hydrolytic reduction. The weight ratio of promoter to catalyst based upon the ruthenium content of the catalyst is within the range of from about 1:0.05 (promoter:catalyst) to about 1:0.10 to about 1:0.015 being preferred.

The hydrolytic reduction is conducted in an aqueous medium with water being the preferred medium. The amount of water can vary widely, but preferably the weight ratio of water to furan is within the range of about 1:4 to about 2:1 (water:furan) with about 1:2 to about 1:1 being more preferred.

As stated above, the reaction is conducted at elevated temperatures and elevated pressures. The temperature is within the range of from about 125° C. to about 175° C., with about 140° C. to about 160° C. being preferred, and with about 150° C. being more preferred. The reaction pressure can vary during the course of the hydrolytic reduction, but is preferably within the range of from about 300 to about 1000 psig, with from about 300 to about 700 psig being preferred, and with about 400 to about 500 psig being more preferred.

The alkanediols may be separated by techniques well known to those skilled in the art, such as, for example, distillation, vacuum distillation (e.g., rotary evaporation) and the like.

Particularly good yields of 1,4-butanediol are obtained when 1.0 g of promoter and 2.5 g of a 5% ruthenium catalyst supported on $Al_2O_3$—$SiO_2$ are utilized per 37.5 g of furan at a temperature of about 150° C. and a reaction pressure of about 400 to about 600 psig in the presence of about 20.5 g of water. Particularly good results are also obtained when the pressure is reduced to about 425 to about 500 psig.

The following examples serve to illustrate this invention and should not be construed as limiting the invention in any way.

GENERAL PROCEDURE

Unless noted otherwise, a 300 mL, autoclave was charged with water (20.5 g), catalyst (5% ruthenium on $Al_2O_3$), acid promoter (1.0 g, trifluoroacetic acid), and furan (37.5 g). The autoclave was flushed twice with approximately 100 psig $H_2$ and then pressure tested at approximately 500 psig $H_2$. The autoclave was then heated to approximately 150° C. with stirring under approximately 500 psig $H_2$. When the temperature of the autoclave reached within 10° C. of 1500, it was charged to approximately 500 psig with $H_2$. The autoclave was cooled with water to prevent a temperature overshoot. When the pressure in the autoclave dropped to approximately 400±50 psig $H_2$, it was recharged to approximately 500±50 psig $H_2$. After approximately one hour, $H_2$ uptake essentially stopped. The autoclave was cooled to approximately 30° C. (e.g., 27° C.–33° C.), and disconnected from the $H_2$ source while still under pressure. The reactor was then cooled for approximately ½ hour in an ice bath, vented and opened. An aliquot of the reaction mixture was centrifuged and a measured amount of supernatant was mixed with a measured amount of cyclohexanol. VPC analysis was conducted on this mixture to determine the relative amounts (in weight %) of the reaction products.

The VPC condition were 10% SE-52, ⅛"×12'; starting temperature 60° C., held for 3 minutes and then brought to 160° C. at 20° per minute and then held at 160° C.

CONTROL

A 300 mL autoclave liner was charged with water, (20.5 g) furan, (37.5 g), and a 5% ruthenium catalyst supported on $Al_2O_3$, (2.5 g). No promoter was used in this reaction. The autoclave was pressure tested at 400 psig $H_2$ and then heated to 150° C. $H_2$ was continually added during the reaction to maintain a pressure of 400–500 psig. After 1.5 hours the $H_2$ uptake stopped. The reaction mixture was cooled to 0° C. in an ice bath and then vented.

VPC analysis showed no 1,4-butanediol product. Other reaction products were tetrahydrofuran, 20.7 g, and n-butanol, 7.3 G. Furan, 8.1 g, was recovered. The carbon-closure was 92 wt % and the conversion was 78.4 wt %.

EXAMPLES 1–7

The results obtained by following the foregoing procedure utilizing the promoters of this invention, Examples 1–4, and promoters not of this invention, comparative Examples 5–7, are reported in Table I. The reaction time was approximately 1 hour. In Table I the following abbreviations are used: Rxn=reaction, BD=1,4-butanediol, THF=tetrahydrofuran, and nBuOH=n-butanol. The yield of 1,4-butanediol (BD) as based upon converted starting furan was determined by the following formula:

$$\frac{\text{Moles BD}}{(\text{conversion})(\text{moles furan})} \times 100$$

wherein the moles of furan is the amount of furan at the start of the reduction process.

The percent conversion is determined by the following formula:

$$(x-y)/x \times 100$$

wherein x is the amount of furan in grams at the start of the reaction and y is the amount of furan left at the end of the reaction.

The percent carbon-closure was determined by the following formula:

$$(p/q) \times 100$$

wherein p is the total number of moles of all products formed in the reaction and q is the moles of furan at the start of the reaction.

TABLE I

| Hydrolytic Reduction of Furan with 5% Ru on $Al_2O_3$ | | | | | | | | |
|---|---|---|---|---|---|---|---|---|
| | Reaction Parameters | | | Results | | | | |
| | Prom. (g) | Temp. (°C.) | Press. (psig) | Conv. (%) | BD (g) | THF (g) | n-BuOH (g) | BD yield (%) | C-Closure (%) |
| Example No. | | | | | | | | | |
| 1 | $F_3CCO_2H$ | 175 | 750–1000 | >99 | 9.2 | 10.5 | 6.9 | 18.5 | 65[3] |
| 2 | $F_3CCO_2H$ | 150 | 400–500 | 96.4 | 13.5 | 15.2 | 5.8 | 28.2 | 85 |
| 3 | $F_3CCO_2H$[1] | 150 | 400–500 | 93.5 | 12.8 | 14.2 | 6.4 | 27.6 | 85 |
| 4 | $F_3CCO_2H$ | 100 | 400–500 | >99 | 3.7 | 32.2 | 4.3 | 7.5 | 99 |
| Comparative Example No. | | | | | | | | | |
| 5 | $H_3PO_4$ | 150 | 400–500 | 94.2 | 1.9 | 23.8 | 9.2 | 4.1 | 93 |
| 6 | $CH_3CO_2H$ | 150 | 400–500 | >99 | 2.3 | 25.2 | 10.9 | 4.6 | 96 |
| 7 | $CH_3CO_2H$[1] | 150 | 450–550 | 95.6 | 5.1 | 21.7 | 10.1 | 10.8 | 96 |

[1]22 mg. stannous chloride ($SnCl_2$) added (Sn:Ru mole ration = 0.1:1)

The data in Table I clearly demonstrate that good yields of 1,4-butanediol were obtained with the promoters of the catalyst/promoter systems of this invention whereas use of promoters not of this invention resulted in poor yields of 1,4-butanediol.

The foregoing disclosure and description of the invention is illustrative and explanatory thereof and various changes in the illustrated process may be made within the scope of the appended claims without departing from the spirit of the invention.

I claim:

1. In a process for producing alkanediols by the hydrolytic reduction of hydrolytically reducible furans at elevated temperatures and elevated pressures using a supported metal catalyst, said alkanediols having the two hydroxy groups resulting from said hydrolytic reduction bonded to different carbon atoms which are separated from each other by two other carbon atoms, the improvement which comprises conducting the hydrolytic reduction in an aqueous medium utilizing a supported ruthenium catalyst, and a trihaloacetic acid or a mixture thereof as a promoter for the hydrolytic reduction.

2. The process of claim 1 wherein said catalyst contains about 0.5 to about 20% by weight of ruthenium.

3. The process of claim 1 wherein said catalyst comprises 5% by weight of ruthenium supported on $Al_2O_3$—$SiO_2$.

4. The process of claim 1 wherein said promoter is trifluoroacetic acid.

5. The process of claim 1 wherein said promoter is trichloroacetic acid.

6. The process of claim 1 wherein said catalyst to said furan weight ratio is within the range of from about 1:3 to about 1:50.

7. The process of claim 1 wherein said promoter to said catalyst weight ratio based upon the ruthenium content of the catalyst is within the range of from about 1:0.05 to about 1:0.25.

8. The process of claim 1 wherein said furan is a hydrocarbyl substituted furan.

9. The process of claim 1 wherein said furan is furan, and said alkanediol is 1,4-butanediol.

10. The process of claim 1 wherein for a predominant time during the course of said hydrolytic reduction said temperature is within the range of from about 125° C. to about 175° C. and said pressure is within the range of from about 300 to about 1000 psig.

11. The process of claim 1 wherein for a predominant time during the course of said hydrolytic reduction said temperature is within the range of from about 140° C. to about 160° C. and said pressure is within the range of about 300 to about 700 psig.

12. The process of claim 11 wherein said temperature is within the range of about 140° C. to about 160° C., and said pressure is within the range of about 400 to about 500 psig.

13. The process of claim 1 wherein said aqueous medium is water and wherein said water to said furan weight ratio is within the range of from about 1:2 to about 1:1.

14. In a process for producing alkanediols by the hydrolytic reduction of hydrolytically reducible furans at elevated temperatures and elevated pressures using a metal catalyst, said alkanediols having the two hydroxy groups resulting from said hydrolytic reduction bonded to different carbon atoms which are separated from each other by two other carbon atoms, the improvement which comprises conducting the hydrolytic reduction in a water medium utilizing a supported ruthenium catalyst containing about 0.5 to about 20% by weight of ruthenium, and trihaloacetic acid or a mixture thereof as promoter for the hydrolytic reduction, said catalyst to said furan weight being in a ratio within the range of from about 1:3 to about 1:50, said promoter to said catalyst being in a weight ratio based upon the ruthenium content of the catalyst within the range of from about 1:0.05 to about 1:0.25, and for a predominant time during the course of said hydrolytic reduction said water to said furan being in a weight ratio within the range of from about 1:4 to about 2:1, said temperature being within the range of from about 125° C. to about 175° C. and said pressure being within the range of from about 300 to about 1000 psig.

15. The process of claim 14 wherein $Al_2O_3$—$SiO_2$ is the support for said catalyst.

16. The process of claim 17 wherein said promoter is trifluoroacetic acid, said furan is furan, said alkanediol is 1,4-butanediol and $Al_2O_3$—$SiO_2$ is the support for said catalyst.

17. The process of claim 14 wherein said promoter is trichloroacetic acid, said furan is furan, said alkanediol is 1,4-butanediol and $Al_2O_3$—$SiO_2$ is the support for said catalyst.

18. In a process for producing a 1,4-butanediol by the hydrolytic reduction of hydrolytically reducible furans at elevated temperature and elevated pressures using a supported metal catalyst, said alkanediols having the two hydroxy groups resulting from said hydrolytic reduction bonded to different carbon atoms which are separated from each other by two other carbon atoms, the improvement which comprises conducting the hydrolytic reduction in a water medium utilizing a supported ruthenium catalyst containing about 5% by weight of ruthenium, and trihaloacetic acid or a mixture thereof as promoter for the hydrolytic reduction, said catalyst to said furan weight being within the range of about 1:7 to about 1:30, said promoter to said catalyst being in a weight ratio based upon the ruthenium content of the catalyst of about 1:0.10 to about 1:0.15, said water to said furan being in a weight ratio within the range of about 1:2 to about 1:1, and for a predominant time during the course of said hydrolytic reduction said temperature being within the range of about 140° C. to about 160° C. and said pressure being within the range of about 400 to about 1000 psig.

19. The process of claim 18 wherein said promoter is trifluoroacetic acid or trichloroacetic acid, said furan is furan, said alkanediol is 1,4-butanediol and $Al_2O_3$—$SiO_2$ is the support for said catalyst.

20. The process of claim 19 wherein the average pressure is within the range of about 400 to about 500 psig.

* * * * *